(12) United States Patent
Smith et al.

(10) Patent No.: US 11,590,078 B2
(45) Date of Patent: Feb. 28, 2023

(54) VIRAL IMMUNOGENIC COMPOSITIONS

(71) Applicants: Henry J. Smith, Temecula, CA (US); James Roger Smith, Temecula, CA (US)

(72) Inventors: Henry J. Smith, Temecula, CA (US); James Roger Smith, Temecula, CA (US)

( * ) Notice: Subject to any disclaimer, the term of this patent is extended or adjusted under 35 U.S.C. 154(b) by 0 days.

(21) Appl. No.: 14/812,114

(22) Filed: Jul. 29, 2015

(65) Prior Publication Data

US 2015/0328305 A1 Nov. 19, 2015

Related U.S. Application Data

(62) Division of application No. 13/566,663, filed on Aug. 3, 2012, now abandoned.

(60) Provisional application No. 61/514,613, filed on Aug. 3, 2011.

(51) Int. Cl.

| | | |
|---|---|---|
| A61K 39/145 | (2006.01) | |
| A61K 9/127 | (2006.01) | |
| C12N 7/00 | (2006.01) | |
| A61K 9/14 | (2006.01) | |
| A61K 9/00 | (2006.01) | |
| A61K 31/713 | (2006.01) | |
| A61K 39/12 | (2006.01) | |
| A61K 39/00 | (2006.01) | |

(52) U.S. Cl.
CPC ............ *A61K 9/127* (2013.01); *A61K 9/0019* (2013.01); *A61K 9/1271* (2013.01); *A61K 9/14* (2013.01); *A61K 31/713* (2013.01); *A61K 39/12* (2013.01); *A61K 39/145* (2013.01); *C12N 7/00* (2013.01); *A61K 9/0073* (2013.01); *A61K 39/00* (2013.01); *A61K 2039/545* (2013.01); *A61K 2039/55505* (2013.01); *A61K 2039/55555* (2013.01); *A61K 2039/55561* (2013.01); *C12N 2760/16134* (2013.01); *C12N 2760/16171* (2013.01)

(58) Field of Classification Search
None
See application file for complete search history.

(56) References Cited

U.S. PATENT DOCUMENTS

| | | | | |
|---|---|---|---|---|
| 6,485,729 B1 * | 11/2002 | Smith | ................ | C07K 14/005 424/210.1 |
| 2003/0113347 A1 | 6/2003 | Cusi et al. | | |
| 2004/0109869 A1 * | 6/2004 | Glenn | ................ | A61K 9/7061 424/185.1 |
| 2006/0029655 A1 * | 2/2006 | Barenholz | ............ | A61K 9/1271 424/450 |
| 2007/0184068 A1 * | 8/2007 | Renner | ................ | A61K 39/39 424/204.1 |
| 2007/0219149 A1 * | 9/2007 | Hasegawa | ............... | A61P 31/04 424/217.1 |
| 2008/0014217 A1 * | 1/2008 | Hanon | ................ | A61K 39/12 424/209.1 |
| 2009/0214638 A1 * | 8/2009 | Wong | ................ | A61K 9/1272 424/450 |
| 2009/0285854 A1 * | 11/2009 | Contorni | ................ | A61P 31/16 424/209.1 |
| 2011/0070298 A1 * | 3/2011 | Mansour | ................ | A61K 9/10 424/450 |
| 2012/0114746 A1 * | 5/2012 | Kwon | ................ | A61K 31/7088 424/450 |
| 2013/0039973 A1 | 2/2013 | Smith et al. | | |

FOREIGN PATENT DOCUMENTS

| | | | | |
|---|---|---|---|---|
| WO | WO-2008152052 A1 * | 12/2008 | ............. | A61K 39/12 |
| WO | 2010/054654 | 5/2010 | | |

OTHER PUBLICATIONS

Conne et al., Immunogenicity of trivalent subunit versus virosome-formulated influenza vaccines in geriatric patients. Vaccine, vol. 15, No. 15, pp. 1675-1679, 1997.*
Jiang et al., Biodegradable poly(lactic-co-glycolic acid) microparticles for injectable delivery of vaccine antigens. Advanced Drug Delivery Reviews 57 (2005) 391-410.*
Joseph et al., Liposomal immunostimulatory DNA sequence (ISS-ODN): an efficient parenteral and mucosal adjuvant for influenza and hepatitis B vaccines. Vaccine 20 (2002) 3342-3354.*
Park et al., The production and immunostimulatory activity of double-stranded CpG-DNA. BMB reports, 2010, 43:164-169.*
Mbawuike et al., Reversal of age-related deficient influenza virus-specific CTL responses and IFN-gamma production by monophosphoryl lipid A.Cell Immunol. Oct. 10, 1996;173(1):64-78.*
Kennedy et al., Dose Sparing with Intradermal Injection of Influenza Vaccine. N Engl J Med 2004;351:2295-301.*
Bresson et al., Safety and immunogenicity of an inactivated split-virion influenza A/Vietnam/1194/2004 (H5N1) vaccine: phase I randomised trial. Lancet 2006; 367: 1657-64.*
R.G. Strickley. Solubilizing Excipients in Oral and Injectable Formulations. Pharmaceutical Research, vol. 21, No. 2, Feb. 2004, pp. 201-230. (Year: 2004).*
Santiago et al., Vaccination with drifted variants of avian H5 hemagglutinin protein elicits a broadened antibody response that is protective against challenge with homologous or drifted live H5 influenza virus. Vaccine. Nov. 8, 2011;29(48):8888-97 (Year: 2011).*

(Continued)

*Primary Examiner* — Arthur S Leonard

(57) ABSTRACT

Disclosed herein are immunogenic compositions for producing immediate and sustained immunity to infectious viral and bacteriological pathogens. A univalent immunogenic composition is disclosed comprising an isolated antigen and a polynucleotide formulated into a nanoparticle or liposome. Furthermore, multivalent immunogenic compositions are disclosed comprising multiple univalent immunogenic compositions. Also disclosed, are methods of inducing protective or therapeutic immune responses in individuals comprising administering one or more univalent immunogenic compositions.

2 Claims, No Drawings

(56) References Cited

OTHER PUBLICATIONS

Stahl-Hennig et al., Synthetic Double-Stranded RNAs Are Adjuvants for the Induction of T Helper 1 and Humoral Immune Responses to Human Papillomavirus in Rhesus Macaques. PLoS Path, 2009, 5:e1000373 (Year: 2009).*

Kenny et al. Dose Sparing with Intradermal Injection of Influenza Vaccine (NEJM, 2004, 351:2295-2301) (Year: 2004).*

Chirigos et al., Vaccine adjuvant effects, and immune response, to synthetic polymers MVE and poly (ICLC). Chemical Regulations of Immunity in Veterinary Medicine, pp. 467-479 (1984).

Grist et al., Haemagglutination and haemagglutination inhibition tests, Diagnostic methods in clinical virology, 2nd ed., Chp. 8, pp. 103-111, Blackwell Scientific Publications, London (197 4).

Harrington et al., Intranasal infection of monkeys with Japanese encephalitis virus: clinical response and treatment with a nuclease-resistant derivative of poly(I):poly(C). Am. J. Trap. Med. Hyg. 26(6) : 1191-1198 (1977).

Hilleman, M. Realities and enigmas of human viral influenza: pathogenesis, epidemiology and control. Vaccine 20: 3068-3087 (2002).

Ichinohe et al., Synthetic double-stranded RNA poly(I:C) combined with mucosal vaccine protects against influenza virus infection. J. Viral. 79 (5): 2910-2919 (2005).

Kende, M. Prophylactic and therapeutic efficacy of poly {I,C)-LC against Rift Valley fever virus infection in mice. J. Bioi. Response Modifiers 4: 503-511 (1985).

Kistner et al., Cell culture (Vera) derived whole-virus (H5N1) vaccine based on wild-type virus strain induces cross-protective immune responses. Vaccine, 25:6028-6036 (2007).

Leroux-Roels et al., Antigen sparing and cross-reactive immunity with an adjuvanted rH5N1 prototype pandemic influenza vaccine: a randomised controlled trial. Lancet, vol. 370 : 580-589 (2007).

Levy et al., A modified polyriboinosinic-polyribocytidylic acid complex that induces interferon in primates. J. Infect. Dis. 132(4): 434-439 (1975).

Potter, CW., A history of infteunza. J. of Appl. Microbial., 2001, 91 : 572-579.

Stephen et al., Protective and toxic effects of a nuclease-resistant derivative of polyriboinosinicpolyribocytidylic acid on Venezuelan equine encephalomyelitis virus in rhesus monkeys. J. Infect. Dis. 139(3): 267-272 (1979).

Stephen et al., Effect of a nuclease-resistant derivative of polyriboinosinic-polyribocytidylic acid complex on yellow fever in rhesus monkeys (*Macaca mulatta*). J. Infect. Dis. 136(1): 122-126 (1977).

Treanor et al., Safety and Immunogenicity of a Baculovirus-Expressed Hemagglutinin Influenza Vaccine: A Randomized Controlled Trial. JAMA, 297(14): 1577-1582 (2007).

Webster et al., Evolution and Ecology of Influenza A Viruses. Microbiological Reviews, vol. 56 (1): 152-179, (1992).

Wiltrout et al., Immunomodulation of natural killer activity by poly-ribonucleotides. J. Bioi. Response Modifiers 4: 512-517 (1985).

Wong et al., Prophylactic and Therapeutic Efficacies of Poly(IC.LC) against Respiratory Influenza A Virus Infection in Mice. Antimicrobial Agents and Chemotherapy vol. 39 (11) : 2574-2576 (1995).

Wong et al., Enhanced protection against respiratory influenza A infection by liposome-encapsulated antibody. Immunology 81 :280-284 (1994).

Wright, P.F. Vaccine Preparedness—Are We Ready for the Next Influenza Pandemic. NEJM, 358 : 2540-2543 (2008).

Hessel et al., Immunostimulatory oligonucleotides block allergic airway inflammation by inhibiting Th2 cell activation and IgE-mediated cytokine induction. J Exp Med., 202(11):1563-73 (2005).

Wenlei Jiang et al., Biodegradable poly(lactic-co-glycolic acid) microparticles for injectable delivery of vaccine antigens. Advanced Drug Delivery Reviews. vol. 57, Issue 3, pp. 391-410 (2005).

* cited by examiner

VIRAL IMMUNOGENIC COMPOSITIONS

CROSS-REFERENCE TO RELATED APPLICATIONS

This application is a divisional of U.S. patent application Ser. No. 13/566,663 filed Aug. 3, 2012, which claims the benefit under 35 U.S.C. § 119(e) to U.S. Provisional Application 61/514,613 filed Aug. 3, 2011, the entire contents of both of which are incorporated by reference herein.

FIELD OF THE INVENTION

The present application is drawn to immunogenic compositions for preventing and treating Influenza virus infection, and methods of making and using the immunogenic compositions.

BACKGROUND OF THE INVENTION

Every year many people catch "the flu" and for most it is a self-limiting illness with recovery occurring between two to three weeks. Influenza is however, a potentially more severe infectious disease which is highly contagious. It is estimated that there are between three to five million cases of severe flu worldwide resulting in up to 500,000 deaths annually. There are two types of influenza viruses that cause epidemic human disease: the Influenza A virus which has many different strains, and the Influenza B virus which consists of a single strain. Current flu vaccines are a mixture of viral antigens prepared from selected strains of influenza A virus and from the single strain of the influenza B virus. The current vaccination programs are aimed at containing the seasonal flu. Health authorities from many countries collaborate with one another to predict the strain of influenza A virus that is likely to cause flu in the upcoming months. For the most part, these types of vaccination programs have worked well to contain the seasonal flu, although they become less effective when the flu epidemic is caused by a different influenza A strain than was predicted. This is because vaccination against one influenza A strain affords little if any immunity against a different influenza A strain. Once the strain is identified it takes about six months to manufacture large quantities of the appropriate vaccine. As such, one of the drawbacks of these vaccination programs is the time it takes to formulate a vaccine which may not even provide any protection against the influenza A strain causing seasonal flu in a particular season. For instance, if it takes six months to formulate a vaccine which provides little or no immunity because the predicted strain is not the one causing the infection, it will take another six months to develop the appropriate vaccine at which point there may be a threat for a major flu pandemic.

It would therefore be desirable to develop an effective immunogenic composition that is tailored to any flu strain that may arise and that can be produced in large quantities and deployed rapidly. Further, it would be desirable if the immunogenic composition could elicit an immediate and prolonged immunity to the flu virus.

The desirability of developing such an immunogenic composition becomes even more urgent when one considers that every ten to twenty years a flu strain arises that infects a large proportion of the world's population and has the potential to kill tens of millions of people. For example, within the last century there have been three major flu pandemics: the Spanish Flu in 1918-1920 which killed 40 million to 100 million people; the Asian Flu in 1957-1958 which killed 1 million to 1.5 million people; and the Hong Kong Flu in 1968-1969 which killed about 1 million people.

Another major obstacle in developing an effective vaccination program is that the influenza A virus is constantly changing. For example, it is known that the influenza A virus may undergo successive point mutations during replication (i.e. genetic drift) and can gradually acquire the capacity over time to become more virulent. Another way in which new strains of flu virus appear is when different flu strains may co-infect a host and exchange genetic information with each other (i.e. genetic shift) resulting in the appearance of a new flu strain with different infective properties and pathogenic potential from either of its parent strains.

Different strains of the influenza A virus are known to infect a variety of animal species, including birds and pigs, and some of these strains may cross specie lines and infect humans. If the infected human also happens to be co-infected with another strain of influenza virus there is a possibility that the two viral strains may exchange genetic information resulting in the appearance of a new strain. For example, there is great concern that the avian flu virus found in domestic and wild birds may infect a human who is carrying a human flu virus strain and exchange genetic information to form a new flu viral strain with the capacity to propagate from human to human resulting in a worldwide pandemic.

There are intensive efforts being made to develop antiviral drugs and vaccines to combat the threat of a worldwide pandemic. Much of the research on flu vaccine is based on traditional methods of growing the virus in embryonated eggs or in tissue cultured cells and then extracting the viral proteins to prepare a vaccine. This has worked fairly well for seasonal flu vaccines where health agencies are able to identify new strains of flu virus as they arise and have sufficient time to prepare the appropriate vaccine. However, the vaccination program still has to be repeated each year as immunity to one strain of the flu virus will not fully protect against any new strain that develops.

Another major obstacle with the traditional vaccination program is that because of mass transit and the large numbers of air travelers, any flu strain that arises in one country can quickly spread among other countries and infect the general population. Moreover, because of the many potential permutations of influenza virus strains that can arise, it is difficult to prepare a vaccine in a timely fashion using the traditional method of growing the virus in embryonated eggs or culturing viral infected cells. Thus, the time frame for identifying new viral strains and preparing large amounts of the correct vaccine has grown increasingly short which continues to be one of the major hindrances facing the traditional vaccination program. There are also very stringent manufacturing safety protocols that must be employed throughout production when a pathogenic virus is used to prepare a vaccine. Even the more recent methods of using genetic engineering to prepare recombinant viral antigens still require several months to prepare a suitable vaccine that may not be deployed in time to be effective.

The current vaccination programs that were developed for the seasonal flu are unable to produce the large quantities of vaccine in the limited time available to protect against a flu pandemic. Even the most current vaccine production methods using cell culture requires about 4 months to produce the appropriate vaccine (Novartis 2008). This time frame is clearly inadequate when the response time required to prevent a flu pandemic is measured in days.

The difficulty is further compounded because the current vaccines are only designed to elicit a classical immune response which can take several weeks to develop after vaccination. Moreover, to develop full immunity two doses of vaccine are often required. For example, The World Health Organization reported in 2007 that "It is unlikely that a potential pandemic could be successfully contained through the use of vaccination alone. Vaccination, with some exceptions, is not normally used to "contain" outbreaks of seasonal influenza. Full immunity is likely to require two doses of vaccine, and to take 3 weeks to develop after the first vaccination. Moreover, the degree of antigenic match between stockpiled vaccine and a potential H5N1 influenza pandemic virus cannot be known. There will also be considerable logistical challenges in vaccinating large numbers (possibly millions) of people over a relatively short period of time."

In view of the deficiencies of the current vaccination programs it would be desirable to develop an immunogenic composition that could provide immediate and long-term immunity to any flu strain that should arise. It would also be desirable to be able to produce large quantities of the appropriate flu immunogenic composition very quickly so that it can be deployed in time to be effective.

SUMMARY OF THE INVENTION

This application discloses a method of preparing a multivalent immunogenic composition against the influenza A virus.

Disclosed herein, is a univalent immunogenic composition comprising an isolated antigen and a polynucleotide formulated into a nanoparticle or liposome.

In one embodiment, the univalent immunogenic composition further comprises an adjuvant. In another embodiment, the adjuvant is alum. In another embodiment, the adjuvant is formulated into the nanoparticle or liposome or admixed with the nanoparticle or liposome formulated univalent immunogenic composition.

In another embodiment, the isolated antigen is an influenza virus antigen such as a hemagglutinin, a neuraminidase, or a matrix protein.

In one embodiment, the polynucleotide is a synthetic polynucleotide comprising double stranded DNA or double stranded RNA. In another embodiment, the double stranded DNA or double stranded RNA comprises nucleotide repeats. In yet another embodiment, the polynucleotide is poly-IC or poly-ICLC.

In another embodiment the liposome is a self-assembling liposome system. In yet another embodiment, the liposome further comprises monophosphoryl lipid A or pullulans.

Also disclosed herein, is a method of inducing a protective or therapeutic immune response in an individual comprising administering one or more univalent immunogenic compositions, wherein a first univalent immunogenic composition comprises a first antigen. In another embodiment, a second univalent immunogenic composition comprises a second antigen. In another embodiment, a third univalent immunogenic composition comprises a third antigen.

In another embodiment, the one or more univalent immunogenic compositions are administered by a method selected from the group consisting of scarification, intradermal injection, intramuscular injection, sub-lingual administration, and inhalation. In other embodiments, the one or more univalent immunogenic compositions are administered at different times or substantially simultaneously. In another embodiment, the one or more univalent immunogenic compositions are each administered by injection to the individual at the same site on the individual or at different sites on the individual. In another embodiment, the one or more univalent immunogenic compositions are combined prior to injection into a multivalent immunogenic composition.

Also disclosed herein, is a multivalent immunogenic composition comprising two or more univalent immunogenic compositions, wherein each of the univalent immunogenic compositions comprises a different antigen.

In yet another embodiment, the approach of stockpiling all the components required to prepare a complete univalent or multivalent immunogenic composition or the univalent immunogenic compositions themselves is disclosed. The components are viral antigen and polynucleotide packaged into a nanoparticle or liposome. Once an epidemic flu virus is identified, the stockpiled immunogenic composition components, or univalent immunogenic compositions, can be quickly assembled into the appropriate univalent immunogenic compositions directed against the identified viral antigens. The selected univalent immunogenic compositions are then administered separately or they may be combined to form a multivalent immunogenic composition before administration.

The same general principles enumerated herein can be applied to preparing immunogenic compositions against other viral and bacterial pathogens. It can be particularly advantageous when applied to vaccination programs against potential pandemics and the threat of bioterrorism.

DETAILED DESCRIPTION OF THE INVENTION

Disclosed herein is a comprehensive integrated approach to developing an effective vaccination program that can be employed to protect against influenza. The same general principles can also be employed to prepare immunogenic compositions against other viral and microbiological pathogens. As used herein, an "immunogenic composition" refers to a composition capable of inducing a protective or therapeutic immune response, with or without an adjuvant, and includes, in part, an antigen against which the protective or therapeutic immune response is elicited. An immunogenic composition is an example of an immunogenic composition.

First, a number of basic univalent immunogenic compositions are prepared with each immunogenic composition directed against a single antigen selected from the group of hemagglutinin (H), neraminidase (N), and matrix (M) antigens of the influenza A virus. An individual's immune response is enhanced by presenting only one purified antigen at a time to an antigen processing and/or immunocompetent cell. Rapid and persistent immunity is achieved by incorporating a double-stranded polynucleotide chain with each specific viral antigen. The combined antigen and polynucleotide moieties are incorporated into a nanoparticle or liposomal univalent immunogenic composition formulation. Administration of the immunogenic composition stimulates an immediate protective interferon response followed by the classical immune response to the antigen. To shorten the response time to the threat of an epidemic, the individual components of the univalent immunogenic composition i.e. viral antigen, polynucleotide, and nanoparticle or liposome supplies are separately stockpiled and stored. Once the suspect flu virus strain is identified the appropriate immunogenic composition components are then assembled into separate univalent immunogenic compositions. Individuals may receive one or more univalent immunogenic compositions directed against different flu antigens to obtain broad immunity. Several different univalent immunogenic compositions may also be combined to produce a multivalent immunogenic composition for convenience in administration. Vaccination may be by dermal, sub-dermal, or intramuscular injection, or by inhalation, or sub-lingual administration.

Further disclosed herein is a method of immunogenic composition preparation that is appropriate for flu immunogenic compositions. The immunogenic composition is designed to confer immediate and long-term protection against viral infection and is particularly useful against pandemic flu viruses. It is also designed to be an effective immunogenic composition by using prestocked components that can be easily formulated into a immunogenic composition and quickly deployed where needed.

The Influenza A Virus

The influenza A virus consists of a viral RNA core surrounded by a viral coat composed of multiple units of hemagglutinin (H) protein and multiple units of neraminidase (N) protein. There are 16 known varieties of H protein and 9 known varieties of the N protein. These are designated as H1 thru H16, and N1 thru N9 respectively. Each strain of flu virus has one H component and one N component making up its viral coat. For example, one avian flu virus is composed of H5N1 one mild strain of human flu was found to be H9N and a virulent strain of human flu was found to be H1N1.

When different strains of flu virus co-infect the same host they may exchange genetic information resulting in a reshuffling of the H and N components to form a new viral strain. For example, if the flu strain H5N1 infects a human who is also infected with a flu virus such as H1N2, it is possible that a new flu strain H5N2 or a new flu strain H1N1 could be created. The new strain will exhibit a different infectivity and virulence profile from its parent strains.

Based on the number of different H antigens and N antigens exhibited by the known influenza A viruses, the total number of permutations that could theoretically result from genetic reshuffling is calculated by multiplying the 16 H varieties by the 9 N varieties to give 144 possible flu strains. In addition there are minor antigenic variations (i.e. clades) that will result in even greater antigenic diversity.

This application discloses that it would be more advantageous to stockpile individual components of the immunogenic composition and to then assemble the final immunogenic composition once the flu strain was identified rather than trying to develop a complete immunogenic composition against a predicted flu strain. This approach eliminates the time required to grow the predicted virus strain and produce large quantities of the immunogenic composition. It also provides a more efficient method of ensuring that the immunogenic composition is specific for the virus. For example, many companies are stockpiling vaccines prepared against the avian flu virus H5N1 because of the possibility that the H5N1 virus strain could become pandemic. But if there was a genetic shift and the pandemic flu virus turned out to be a H1N1 strain instead, the H5N1 immunogenic composition would not provide immunity against the H1N1 virus. However, if there were stockpiles of the H1 antigen and the N1 antigen as disclosed herein, then a multivalent immunogenic composition composed of a H1 univalent immunogenic composition and N1 univalent immunogenic composition would be available and expected to provide better protection as they would be targeted against the appropriate strains causing the virus. Further, the stockpiled immunogenic composition components can be assembled very quickly and be deployed in an effective time to where they are needed.

It should also be noted that there are antigenic variations within each type of isolated influenza A strain. For example, the H5 antigen of the H5N1 virus will show antigenic differences between different H5N1 isolates. In developing an immunogenic composition those H5 antigenic subtypes are selected which show the best cross-reactivity with other H5 isolates and/or develop several immunogenic compositions directed against selected antigenic sub-types. This also applies for other influenza A strains that exhibit antigen variation within the strain.

In another embodiment of this disclosure, the immunogenic composition also includes a purified antigen prepared from the conserved matrix (M1 and M2) regions of the flu virus coat.

In order to obtain the best immune response the viral antigens are utilized in a purified and isolated form and each viral antigen is presented separately to the antigen processing and/or immunocompetent cells. In this manner each clone of immunocompetent cells is programmed to react to only a particular antigen.

In order to obtain optimum immunity against a particular flu strain several of these univalent immunogenic compositions directed against different antigens of that strain are used to vaccinate the individual. For convenience and efficiency, the selected univalent immunogenic compositions are optionally combined to form a multivalent immunogenic composition prior to vaccination.

Viral Antigen

In order to prepare a viral antigen, the different H, N and M viral antigens are purified from viral cultures. In one embodiment, the antigens are prepared from cultured viruses. First, a selected strain of influenza A virus is used to inoculate embryonated eggs or cell cultures. After a period of multiplication the virus is extracted from the culture medium and purified using standard production techniques such as chromatography. After inactivation, the viral antigens are separated from other viral components using standard purification methods. The method of culturing the virus and the preparation of purified viral protein is known to those skilled in the art. The methods of antigen purification such as gel-filtration, affinity chromatography and other methods are known to those skilled in the art.

In another embodiment, the purified antigens are prepared by genetic engineering techniques. The genetic code of the particular viral antigen is incorporated into the genomic DNA of a transfected host cell. And the transfected cell is induced to express the corresponding H or N or M viral protein. Non-limiting examples of host cells suitable for production of the viral antigens disclosed herein include bacteria, yeast, insects, mammalian, or plant cells. For example, if the H1 viral antigen was selected, then the genetic code for H1 would be prepared and used to transform a host cell and the H1 antigen is produced as a recombinant protein. The expression level of the recombinant protein is increased by the use of suitable promoter genes. The recombinant antigen is purified by downstream processing and prepared for long term storage by lyophilization, or freezing or other similar processes. The method of genetic engineering and downstream processing are known to those skilled in the art.

In one embodiment, the antigens are prepared using the Baculovirus vector expression system in insect cells or larvae of the silkworm *Bombyx mori*. In this system the genetic code for the viral antigen is linked to the polyhedron promoter gene and used to produce a transformed baculovirus. When the transformed baculovirus is used to infect *Bombix mori* cells they are induced to express the recombinant viral antigen. Similarly, silkworm larvae infected with the transformed baculovirus are induced to produce large amounts of viral antigen in their hemolymph. This method of baculovirus expression of recombinant proteins and downstream processing is known to those skilled in the art. The use of silkworms as inexpensive "bioreactors" to produce large quantities of viral antigen is especially suited for developing countries that do not have access to the advanced and expensive vaccine production capacity of industrialized nations.

The viral antigen is isolated and substantially purified such that only the desired antigen is present in the composition, excluding undesirable antigens, proteins, lipids, or carbohydrates present in the starting material. For the purposes of the present disclosure, the term antigen includes full length proteins, and epitopes or fragments of the full length proteins which maintain the appropriate immunogenicity or ability to stimulate an immune response.

Polynucleotide

This application discloses the inclusion of a polynucleotide into the immunogenic composition. Polynucleotides are molecular chains of nucleotides usually deoxyribonucleic acid (DNA) or ribonucleic acid (RNA). They can be of cellular or viral origin or they can be synthesized. When administered to an individual the polynucleotide has two important functions. First, it has an immune stimulating effect, and second it stimulates the production of interferons which are compounds known to have an inhibitory effect upon viral infections. For maximum anti-viral effect the polynucleotide is typically double-stranded DNA (dsDNA) or double stranded RNA (dsRNA).

Interferons belong to the large class of glycoproteins known as cytokines. They are natural proteins produced by the cells of the immune system in response to challenges by foreign agents such as viruses, parasites and tumor cells. Interferons are produced by a wide variety of cells in response to the presence of double-stranded RNA, a key indicator of viral infection. Interferons assist the immune response by inhibiting viral replication within host cells, activating natural killer cells and macrophages, increasing antigen presentation to lymphocytes, and inducing the resistance of host cells to viral infection. When the antigen is presented to matching T and B cells, those cells multiply, attack and degrade the infectious agent. As disclosed herein presenting the polynucleotide simultaneously with the antigen to the same antigen processing or immunocompetent cell potentiates the immune response in addition to inducing the production of interferons.

In one embodiment of this disclosure a natural dsRNA polynucleotide extracted from any number of known viral or bacterial agents is used. Such agents include influenza A virus, influenza B virus, Sendai virus, *E. coli* etc. The methods of extraction, amplification using polymerase chain reaction (PCR), and purification of the natural polynucleotide are known to those of skill in the art. A synthetic polynucleotide can also be used. According to this disclosure exemplary synthetic polynucleotides are double stranded nucleic acids selected from the group consisting of: polyinosinic acid and polycytidylic acid (poly-IC), polyadenylic acid and polyuridylic acid (poly-AU), polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue.

The polynucleotide chain may be modified by substituting other bases into the chain at specified intervals or by attaching additional compounds such as poly-L-lysine carboxymethylcellulose to the nucleotide chain. For example poly-IC can be stabilized by adding poly-L-lysine to form a new polynucleotide termed poly-ICLC. Poly-ICLC has shown anti-viral protection against a variety of viruses including vaccinia, hepatitis, influenza, herpesvirus, rabies, Japanese encephalitis, West Nile virus, Ebola virus, and HIV. Of particular note is that intranasal poly-ICLC administration can protect mice for as long as 3 weeks from an otherwise lethal dose of influenza virus.

In preparing the univalent immunogenic compositions of the present disclosure, the polynucleotide is mixed with the viral antigen so that both moieties are presented simultaneously to the same antigen processing and/or immunocompetent cell. The ratio of antigen to polynucleotide used in the univalent immunogenic composition may range from the order of 100:1 to 1:100. Depending on its potency the total amount of viral antigen used per univalent immunogenic composition is expected to be within the range of 1 µg to 100 µg per dose.

In aspects of this embodiment, an immunogenic composition disclosed herein may include a dose of viral antigen that is, e.g., 90-100 µg, 80-90 µg, 70-80 µg, 60-70 µg, 50-60 µg, 40-50 µg, 30-40 µg, 20-30 µg, 10-20, or less than 10 µg, less than 20 µg, less than 30 µg, less than 40 µg, less than 50 µg, less than 60 µg, less than 70 µg, less than 80 µg, less than 90 µg, or less than 100 µg. In other embodiments, the ratio of antigen to polynucleotide in the univalent immunogenic composition is, e.g., 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70. 1:75, 1:80, 1:85, 1:90, 1:95, or 1:100.

Immunogenic Composition

The immunogenic composition is prepared by combining a viral antigen and polynucleotide and assembling them into a nanoparticle or liposome. To prepare the immunogenic composition, the viral antigen and polynucleotide are bound to the surface of a solid particle matrix such as colloidal gold particles, chitin nanoparticles, or other similar nanoparticles. The immunogenic composition components may also be incorporated into solid lipid nanoparticles. The methods of preparing nanoparticles include precipitation, homogenization and crystallization methods and are known to those skilled in the art.

In another embodiment, the coated nanoparticles are administered in conjunction with an adjuvant to enhance their uptake by antigen processing cells. Additionally, the coated nanoparticles may be incorporated into an oil-in-water emulsion which has a known adjuvant effect. Suitable adjuvants are known to persons of ordinary skill in the art.

The immunogenic composition may also be prepared in the form of liposomes which are composed of an aqueous core and an outer lipid bilayer membrane. Liposomes are prepared using different lipid compositions. For example, they are prepared using a mixture of one or more of the following compounds: phosphatidylcholine, phosphatidylethanolamine, phosphatidylglycerol, phosphatidylinsitol, monosialoganglioside, sphingomyelin, distearoylphosphatidylethanolamine, distearoylphosphatidylcholine, dimyristoyl-phosphatidylcholine, dimyristoylphosphatidylglycerol, dipalmitoylphosphatidylcholine and the like. Cholesterol is also often included to stabilize the bilayer lipid membrane. The mixed lipids are dissolved in a solvent such as chloroform and dried under vacuum to form a lipid film. The dried lipid film is hydrated in a solution in which the viral antigen and polynucleotide are dissolved. The hydrated lipids will form liposomes entrapping the viral antigen and polynucleotide within the aqueous center of the liposome. Depending on the mixture of lipids used to prepare the liposomes and the method employed, such as freeze/thawing or homogenization or sonication, the liposomes formed may be multilamella or unilamella, and they may range in size from several thousand nanometers in diameter to below one hundred nanometers in diameter. The methods of preparing liposomes are known to those skilled in the art.

In another embodiment of this disclosure, a lipid formulation mixture is employed that will spontaneously form liposomes when mixed with an aqueous solution. The methods of manufacturing self-assembling liposomes are known to those skilled in the art.

In yet another embodiment of this disclosure the outer layer of liposomes may incorporate a known lipid adjuvant such as monophosphoryl lipid A (MPL). The basic liposome formulation will consist of a phospholipid compound such as phosphatidylcholine, cholesterol and MPL.

In another embodiment, a self-assembling liposome formulation incorporates an immune stimulating polysaccharide compound such as pullulans. The pullulans compound is anchored into the liposome membrane layer and stimulates uptake by the dendritic cells of the immune system. The dendritic cells are antigen processing cells responsible for initiating the immune response.

Also within the scope of the present disclosure are kits containing one or more univalent immunogenic compositions, the components for one or more immunogenic compositions, and instructions for use.

In one embodiment, the kit contains two, three, four or more isolated and purified viral antigens, polynucleotides and reagents to prepare two, three, four or more univalent immunogenic compositions. In some embodiments, the kits also contain an appropriate adjuvant.

In another embodiment, the kit contains two, three, four or more univalent immunogenic compositions. In some embodiments, the kits also contain an appropriate adjuvant.

Vaccine Administration

The mode of administration of the immunogenic composition may be by a route including scarification, or by injection, or by inhalation. In one embodiment, each univalent immunogenic composition is administered separately so that the antigen processing cells upon arrival at each site of administration will become programmed to develop immunity to only that particular antigen. In another embodiment, multiple univalent immunogenic compositions are administered in combination or simultaneously injected at different locations.

In order to obtain broader immunity to a viral strain it may be desirable to vaccinate with multiple viral antigens of that strain. For example, if the viral strain was avian flu virus with the H5N1 antigenic makeup, the vaccination program would administer two or more immunogenic compositions given to the individual. One immunogenic composition incorporates the recombinant H5 antigen plus a polynucleotide, a second immunogenic composition incorporates the recombinant N1 antigen plus the polynucleotide, while a third immunogenic composition incorporates the recombinant M antigen plus the polynucleotide. The individual injection sites may be placed close to one another (e.g. using a multineedle injector) or they may be spaced widely apart (e.g. on different arms); or be given at different times (e.g. on different days). The individual immunogenic compositions may also be mixed to prepare a multivalent immunogenic composition and diluted sufficiently so that each antigen processing cell is predominantly exposed to only one antigen. The same rationale for preparing tailor-made immunogenic compositions would apply to other influenza strains whose antigenic identity is known. Similarly for inhalation or sub-lingual administration, each immunogenic composition preparation can be given at different times or on different days.

Example of a Vaccine to Treat Pandemics

For illustrative purposes the preparation of a model immunogenic composition to treat an influenza A pandemic is disclosed herein.

The first step is to identify the strains of influenza A virus that pose the greatest threat of causing a pandemic. These will be the viral strains that are known to infect humans. Specifically, the H, N, and M subtype of the virus is determined.

The hemagglutinin (H) antigen is responsible for the first phase of infection which is the attachment of the virus to the cell; while the neuraminidase (N) antigen is responsible for the last phase of infection which is to cleave and release the viral particle from the infected cell. Therefore an immunogenic composition prepared against the H antigen is more effective in preventing viral infection, while a immunogenic composition prepared against the N antigen is more effective in limiting the transmission of the virus from host to host.

Based on this reasoning the most important antigens for preparing the immunogenic composition will be the hemagglutinin antigen sub-types that show the highest virulence and capacity for human to human transmission.

To increase host immunity to infection and to limit viral spread, immunogenic compositions against the N antigens from viral strains known to infect humans are also included.

Again, for illustrative purposes only, the preparation of a model immunogenic composition against the avian flu virus using selected embodiments is disclosed herein. For an avian flu virus with an H5N1 antigenic makeup, two univalent immunogenic compositions are prepared. One immunogenic composition is directed against the H5 antigen subtype and the other immunogenic composition against the N1 antigen. In this example, the recombinant H5 and N1 proteins are expressed in silkworm larvae using the baculovirus expression system. Briefly, the gene for the H5 protein is in-frame fused with the polyhedrin (Ph) gene under the control of Ph promoter and used to co-transfect cultured BmN cells with modified linearized *Bombyx mori* baculovirus DNA to produce recombinant virus (rBacPh-H5). The recombinant rBacPh-H5 virus is used to infect silkworm larvae which are induced to produce large quantities of recombinant H5 protein in the hemolymph. Similarly, the gene for the N1 protein is in-frame fused with the gene under the control of Ph promoter and used to co-transfect cultured BmN cells with modified linearized *Bombyx mori* baculovirus DNA to produce recombinant virus (rBacPh-N1). The recombinant rBacPh-N1 virus is used to infect silkworm larvae which are induced to produce large quantities of recombinant N1 protein in the hemolymph. The recombinant H5 and N1 proteins are purified using conventional laboratory techniques and stored lyophilized until required.

In this embodiment example, the polynucleotide used in the univalent immunogenic composition is the synthetic polynucleotide poly-ICLC which is a potent immunomodulating agent. The methods of preparing synthetic polynucleotides are known to those skilled in the art. The polypeptide chain can be prepared in bulk and stored in a suitable manner until required.

In this example, a self-assembling liposome incorporating the adjuvant compound is selected to prepare the univalent immunogenic composition. The liposome components such as phosphatidylcholine, cholesterol and adjuvant are premixed in bulk, vacuum-dried and stored frozen until required. Upon addition of an aqueous solution of the premixed viral antigen and polynucleotide the hydrated lipids will spontaneously form liposomes enclosing the antigen and polynucleotide within. The formed liposomes are lyophilized with a cryoprotectant agent and stored in bulk until required.

Other Applications

The concept of stockpiling immunogenic composition components can also be applied to seasonal flu where a univalent immunogenic composition prepared against the influenza B virus can be combined with the univalent immunogenic compositions prepared against the influenza A virus strains to give broad protection against developing the flu.

Disclosed herein is an integrated approach to developing an effective immunogenic composition for pandemic influenza and other viruses capable of causing a pandemic. The elements consist of: 1) producing and stockpiling recombinant viral antigens; 2) producing and stockpiling a selected double-stranded polynucleotide; 3) producing and stockpiling materials to make nanoparticles or liposomes; 4) assembling the recombinant viral antigen and polynucleotide into a univalent immunogenic composition; 5) administering different univalent immunogenic compositions to elicit a sustained immune response; and 6) combining different univalent immunogenic compositions to make a multivalent immunogenic composition to facilitate mass vaccination.

The same general principles enumerated here can be applied to preparing immunogenic compositions against a variety of other viral and bacterial pathogens. There are many known infectious pathogens that are capable of causing pandemics with significant morbidity. The WHO Epidemic and Pandemic Alert and Response list includes: anthrax, avian influenza, Crimean-Congo haemorrhagic fever, dengue haemorrhagic fever, Ebola haemorrhagic fever, hepatitis, influenza, Lassa fever, Marburg haemorrhagic fever, meningococcal disease, plague, rift valley fever, severe acute respiratory syndrome (SARS), smallpox, tularaemia, and yellow fever.

There is also the threat of bioterrorism wherein infectious agents can be modified to make them more infectious and virulent. The most effective means to prepare for these threats is to develop a vaccination program that is effective, safe and can be rapidly deployed.

The above descriptions are given by way of example, and not limitation. Given the above disclosures, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments described in this invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of vaccination for influenza A virus by preparing two discrete liposomal vaccines; and concurrently vaccinating each person exposed to viral infection with said discrete liposomal vaccines wherein:
   (i) the first liposomal vaccine is composed of a purified recombinant hemagglutinin (H) antigen sub-type corresponding to the H antigenic sub-type of the identified virus strain, combined with either poly IC or poly ICLC within a liposome; and wherein monophosphoryl lipid A is optionally incorporated in the lipid layer of the liposome and
   (ii) the second liposomal vaccine is composed of a purified recombinant neuraminidase (N) antigen sub-type corresponding to the N antigenic sub-type of the identified virus strain, combined with either poly IC or poly ICLC within a liposome; and wherein monophosphoryl lipid A is optionally incorporated in the lipid layer of the liposome and
   (iii) all the components required to prepare each of the first and second vaccines were made beforehand and stockpiled to enable the rapid preparation of each vaccine; and wherein said vaccine components included a panel of recombinant H antigen subtypes; a panel of recombinant N antigen subtypes; Poly IC; Poly ICLC; monophosphoryl lipid A, cholesterol, and one or more phospholipids selected from a list of: phosphatidylcholine, phosphatidylethanolamine, phosphatidylglycerol, phosphatidylinositol, monosialoganglioside, sphingomyelin, distearoylphosphatidylethanolamine, distearoylphosphatidylcholine, dimyristoylphosphatidylcholine, dimyristoylphosphatidylglycerol and dipalmitoylphosphatidylcholine.

2. A method of vaccination for influenza A virus according to claim 1 wherein the method of administering each of the two discrete liposomal vaccines disclosed in claim 1 is selected from the group consisting of scarification, intradermal injection, and intramuscular injection, and wherein the H antigen sub-type vaccine is administered at a different anatomical location from the N antigen sub-type vaccine either in separate sites on the same arm, or administering one vaccine in one arm and the other vaccine in the other arm.

* * * * *